(12) United States Patent
Freitag et al.

(10) Patent No.: US 7,631,642 B2
(45) Date of Patent: Dec. 15, 2009

(54) TRACHEOSTOMA SPACER, TRACHEOTOMY METHOD, AND DEVICE FOR INSERTING A TRACHEOSTOMA SPACER

(75) Inventors: Lutz Freitag, Hemer (DE); Anthony Wondka, Thousand Oaks, CA (US)

(73) Assignee: Breathe Technologies, Inc., San Ramon, CA (US)

( * ) Notice: Subject to any disclaimer, the term of this patent is extended or adjusted under 35 U.S.C. 154(b) by 0 days.

(21) Appl. No.: 11/798,965

(22) Filed: May 18, 2007

(65) Prior Publication Data

US 2008/0029088 A1 Feb. 7, 2008

Related U.S. Application Data

(60) Provisional application No. 60/801,104, filed on May 18, 2006.

(51) Int. Cl.
*A61M 11/00* (2006.01)
(52) U.S. Cl. .............................. 128/200.26; 128/207.29
(58) Field of Classification Search ............ 128/207.29, 128/207.14, 200.26
See application file for complete search history.

(56) References Cited

U.S. PATENT DOCUMENTS

| | | | |
|---|---|---|---|
| 2,947,938 A | 8/1960 | Bennett | |
| 3,267,935 A | 8/1966 | Andreasen et al. | |
| 3,357,427 A | 12/1967 | Wittke et al. | |
| 3,493,703 A | 2/1970 | Finan | |
| 3,610,247 A | 10/1971 | Jackson | |
| 3,721,233 A * | 3/1973 | Montgomery et al. .. | 128/207.14 |
| 3,741,208 A | 6/1973 | Jonsson et al. | |
| 3,794,026 A | 2/1974 | Jacobs | |
| 3,961,627 A | 6/1976 | Ernst et al. | |
| 3,991,790 A | 11/1976 | Russell | |
| 4,003,377 A | 1/1977 | Dahl | |
| 4,067,328 A | 1/1978 | Manley | |
| 4,231,365 A | 11/1980 | Scarberry | |
| 4,261,355 A | 4/1981 | Glazener | |

(Continued)

FOREIGN PATENT DOCUMENTS

CA 2535450 2/2005

(Continued)

OTHER PUBLICATIONS

International Search Report and Opinion for Application No. PCT/US07/17400, dated Apr. 28. 2008.

(Continued)

*Primary Examiner*—Steven O Douglas
(74) *Attorney, Agent, or Firm*—Michele V. Frank; Patton Boggs LLP (57) ABSTRACT

The invention relates to a tracheostoma spacer with a tubular support framework. The support framework can be expand from an initial state to a supporting state of increased diameter and has a fixing element at the ends. The tracheostoma spacer is intended for use as a spacer in a tracheostoma (an opening in the trachea). The invention further relates to a device for inserting a tracheostoma spacer into a tracheostoma with a cutting instrument in the form of a trocar, the tracheostoma spacer being able to be positioned on the shaft of said trocar. A cover sleeve is also provided which can be moved on the shaft over a tracheostoma spacer positioned there.

54 Claims, 7 Drawing Sheets

U.S. PATENT DOCUMENTS

| | | |
|---|---|---|
| 4,265,237 A | 5/1981 | Schwanbom et al. |
| 4,274,162 A | 6/1981 | Joy et al. |
| 4,413,514 A | 11/1983 | Bowman |
| 4,449,523 A | 5/1984 | Szachowicz et al. |
| 4,481,944 A | 11/1984 | Bunnell |
| 4,488,548 A | 12/1984 | Agdanowski |
| 4,506,667 A | 3/1985 | Ansite |
| 4,527,557 A | 7/1985 | DeVries et al. |
| 4,535,766 A | 8/1985 | Baum et al. |
| 4,537,188 A | 8/1985 | Phuc |
| 4,630,606 A | 12/1986 | Weerda et al. |
| 4,644,947 A | 2/1987 | Whitwam et al. |
| 4,744,356 A | 5/1988 | Greenwood |
| 4,747,403 A | 5/1988 | Gluck et al. |
| 4,773,411 A | 9/1988 | Downs |
| 4,813,431 A | 3/1989 | Brown |
| 4,825,859 A | 5/1989 | Lambert |
| 4,832,014 A | 5/1989 | Perkins |
| 4,838,255 A | 6/1989 | Lambert |
| 4,850,350 A | 7/1989 | Jackson |
| 4,865,586 A | 9/1989 | Hedberg |
| 4,869,718 A | 9/1989 | Brader |
| 4,905,688 A | 3/1990 | Vicenzi et al. |
| 4,938,212 A | 7/1990 | Snook et al. |
| 4,967,743 A | 11/1990 | Lambert |
| 5,000,175 A | 3/1991 | Pue |
| 5,002,050 A | 3/1991 | McGinnis |
| 5,022,394 A | 6/1991 | Chmielinski |
| 5,024,219 A | 6/1991 | Dietz |
| 5,038,771 A | 8/1991 | Dietz |
| 5,048,515 A | 9/1991 | Sanso |
| 5,054,484 A | 10/1991 | Hebeler, Jr. |
| 5,058,580 A | 10/1991 | Hazard |
| 5,090,408 A | 2/1992 | Spofford et al. |
| 5,101,820 A | 4/1992 | Christopher |
| 5,127,400 A | 7/1992 | DeVries et al. |
| 5,134,995 A | 8/1992 | Gruenke et al. |
| 5,134,996 A | 8/1992 | Bell |
| 5,148,802 A | 9/1992 | Sanders et al. |
| 5,161,525 A | 11/1992 | Kimm et al. |
| 5,181,509 A | 1/1993 | Spofford et al. |
| 5,184,610 A | 2/1993 | Marten et al. |
| 5,186,167 A | 2/1993 | Kolobow |
| 5,193,533 A | 3/1993 | Body et al. |
| 5,217,008 A | 6/1993 | Lindholm |
| 5,233,979 A | 8/1993 | Strickland |
| 5,239,994 A | 8/1993 | Atkins |
| 5,243,972 A | 9/1993 | Huang |
| 5,255,675 A | 10/1993 | Kolobow |
| 5,258,027 A | 11/1993 | Berghaus |
| 5,271,388 A | 12/1993 | Whitwam et al. |
| 5,279,288 A | 1/1994 | Christopher |
| 5,287,852 A | 2/1994 | Arkinstall et al. |
| 5,303,700 A | 4/1994 | Weismann et al. |
| 5,331,995 A | 7/1994 | Westfall et al. |
| 5,339,809 A | 8/1994 | Beck, Jr. et al. |
| 5,368,017 A | 11/1994 | Sorenson et al. |
| 5,400,778 A | 3/1995 | Jonson et al. |
| 5,419,314 A | 5/1995 | Christopher |
| 5,438,980 A | 8/1995 | Phillips |
| 5,460,613 A | 10/1995 | Ulrich et al. |
| 5,474,062 A | 12/1995 | DeVires et al. |
| 5,485,850 A | 1/1996 | Dietz |
| 5,507,282 A | 4/1996 | Younes et al. |
| 5,513,628 A | 5/1996 | Coles et al. |
| 5,535,738 A | 7/1996 | Estes et al. |
| 5,542,415 A | 8/1996 | Brody |
| 5,546,935 A | 8/1996 | Champeau |
| 5,549,106 A | 8/1996 | Gruenke et al. |
| 5,558,086 A | 9/1996 | Smith et al. |
| 5,598,840 A | 2/1997 | Iund et al. |
| 5,669,380 A | 9/1997 | Garry et al. |
| 5,676,132 A | 10/1997 | Tillotson et al. |
| 5,687,714 A | 11/1997 | Kolobow et al. |
| 5,690,097 A | 11/1997 | Howard et al. |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,740,796 A | 4/1998 | Skog |
| 5,762,638 A * | 6/1998 | Shikani et al. ............... 604/265 |
| 5,791,337 A | 8/1998 | Coles et al. |
| 5,819,723 A | 10/1998 | Joseph |
| 5,865,173 A | 2/1999 | Froehlich |
| 5,904,648 A | 5/1999 | Arndt et al. |
| 5,906,204 A | 5/1999 | Beran et al. |
| 5,911,756 A | 6/1999 | Debry |
| 5,918,597 A | 7/1999 | Jones et al. |
| 5,928,189 A | 7/1999 | Phillips et al. |
| 5,931,162 A | 8/1999 | Christian |
| 5,937,853 A | 8/1999 | Ström |
| 5,954,050 A | 9/1999 | Christopher |
| 5,964,223 A | 10/1999 | Baran |
| 5,975,077 A | 11/1999 | Hofstetter et al. |
| 5,975,081 A | 11/1999 | Hood et al. |
| 6,039,696 A | 3/2000 | Bell |
| 6,105,575 A | 8/2000 | Estes et al. |
| 6,109,264 A * | 8/2000 | Sauer .................... 128/207.29 |
| 6,152,132 A | 11/2000 | Psaros |
| 6,213,119 B1 | 4/2001 | Brydon et al. |
| 6,220,244 B1 | 4/2001 | McLaughlin |
| 6,227,200 B1 | 5/2001 | Crump et al. |
| 6,305,374 B1 | 10/2001 | Zdrojkowski et al. |
| 6,315,739 B1 | 11/2001 | Merilainen et al. |
| 6,345,619 B1 | 2/2002 | Finn |
| 6,357,438 B1 | 3/2002 | Hansen |
| 6,378,520 B1 | 4/2002 | Davenport |
| 6,427,690 B1 | 8/2002 | McCombs et al. |
| 6,439,228 B1 | 8/2002 | Hete et al. |
| 6,450,164 B1 | 9/2002 | Banner et al. |
| 6,457,472 B1 | 10/2002 | Schwartz et al. |
| 6,520,176 B1 | 2/2003 | Dubois et al. |
| 6,520,183 B2 | 2/2003 | Amar |
| 6,532,960 B1 | 3/2003 | Yurko |
| 6,568,391 B1 | 5/2003 | Tatarek et al. |
| 6,571,796 B2 | 6/2003 | Banner et al. |
| 6,575,944 B1 | 6/2003 | McNary et al. |
| 6,588,422 B1 | 7/2003 | Berthon-Jones et al. |
| 6,609,517 B1 | 8/2003 | Estes et al. |
| 6,626,175 B2 | 9/2003 | Jafari et al. |
| 6,629,527 B1 | 10/2003 | Estes et al. |
| 6,629,529 B2 | 10/2003 | Arnott |
| 6,640,806 B2 | 11/2003 | Yurko |
| 6,655,382 B1 | 12/2003 | Kolobow |
| 6,666,208 B1 * | 12/2003 | Schumacher et al. ... 128/200.24 |
| 6,668,829 B2 | 12/2003 | Biondi et al. |
| 6,694,978 B1 | 2/2004 | Bennarsten |
| 6,705,314 B1 | 3/2004 | O'Dea |
| 6,722,360 B2 | 4/2004 | Doshi |
| 6,722,362 B2 | 4/2004 | Hete et al. |
| 6,752,151 B2 | 6/2004 | Hill |
| 6,758,217 B1 | 7/2004 | Younes et al. |
| 6,810,876 B2 | 11/2004 | Berthon-Jones |
| 6,814,073 B2 | 11/2004 | Wickham |
| 6,814,077 B2 | 11/2004 | Elstert |
| 6,823,866 B2 | 11/2004 | Jafari et al. |
| 6,840,240 B1 | 1/2005 | Berthon-Jones et al. |
| 6,854,462 B2 | 2/2005 | Berthon-Jones et al. |
| 6,877,511 B2 | 4/2005 | DeVries et al. |
| 6,910,480 B1 | 6/2005 | Berthon-Jones |
| 6,910,482 B2 | 6/2005 | Bliss et al. |
| 6,913,601 B2 | 7/2005 | St. Goar et al. |
| 6,915,803 B2 | 7/2005 | Berthon-Jones et al. |
| 6,920,878 B2 | 7/2005 | Sinderby et al. |

| | | | | | | |
|---|---|---|---|---|---|---|
| 6,932,084 B2 | 8/2005 | Estes et al. | | EP | 0125424 | 11/1984 |
| 6,941,950 B2 | 9/2005 | Wilson et al. | | EP | 0692273 | 1/1996 |
| 6,948,497 B2 | 9/2005 | Zdrojkowski et al. | | EP | 0778035 | 6/1997 |
| 6,951,217 B2 | 10/2005 | Berthon-Jones | | EP | 1654023 | 5/2006 |
| 6,971,382 B1 * | 12/2005 | Corso .................. 128/200.26 | | EP | 07836502.0 | 2/2008 |
| 6,997,881 B2 | 2/2006 | Green et al. | | EP | 1926517 | 6/2008 |
| 7,000,612 B2 | 2/2006 | Jafari et al. | | EP | 2023987 | 2/2009 |
| 7,011,091 B2 | 3/2006 | Hill et al. | | IN | 317/KOLNP/06 | 3/2007 |
| 7,017,574 B2 | 3/2006 | Biondi et al. | | IN | 1105/KOLNP/2008 | 3/2008 |
| 7,044,129 B1 | 5/2006 | Truschel et al. | | IN | IN 6979/CHEN/2008 | 12/2008 |
| 7,066,173 B2 | 6/2006 | Banner et al. | | JP | 2002-204830 | 7/2002 |
| 7,077,132 B2 | 7/2006 | Berthon-Jones | | JP | 2006-522883 | 2/2007 |
| 7,080,646 B2 | 7/2006 | Wiesmann et al. | | JP | 2009-511111 | 5/2007 |
| 7,100,607 B2 | 9/2006 | Zdrojkowski et al. | | JP | 2009-508645 | 3/2009 |
| 7,121,277 B2 | 10/2006 | Ström | | WO | WO-98/01176 | 1/1998 |
| 7,152,598 B2 | 12/2006 | Morris et al. | | WO | WO-01/76655 | 10/2001 |
| 7,156,090 B2 | 1/2007 | Nomori | | WO | WO-2005/014091 | 2/2005 |
| 7,195,016 B2 * | 3/2007 | Loyd et al. ............. 128/207.14 | | WO | WO-2007/035804 | 3/2007 |
| 7,222,623 B2 | 5/2007 | DeVries et al. | | WO | WO-2007/142812 | 12/2007 |
| 7,255,103 B2 | 8/2007 | Bassin | | WO | PCT/US2007/017400 | 2/2008 |
| 7,267,122 B2 | 9/2007 | Hill | | WO | WO-2008/019102 | 2/2008 |
| 7,270,128 B2 | 9/2007 | Berthon-Jones et al. | | WO | WO 2008/144589 | 11/2008 |
| 7,296,573 B2 | 11/2007 | Estes et al. | | WO | WO 2008/144669 | 11/2008 |
| 7,373,939 B1 * | 5/2008 | DuBois et al. ......... 128/207.29 | | WO | PCT/US2009/041027 | 4/2009 |
| 7,487,778 B2 | 2/2009 | Freitag | | WO | PCT/US2009/041034 | 4/2009 |
| 2001/0035185 A1 | 11/2001 | Christopher | | WO | WO 2009/042973 | 4/2009 |
| 2002/0179090 A1 | 12/2002 | Boussignac | | WO | WO 2009/042974 | 4/2009 |
| 2003/0121519 A1 | 7/2003 | Estes et al. | | | | |
| 2003/0145853 A1 | 8/2003 | Muellner | | | | |
| 2003/0145856 A1 | 8/2003 | Zdrojkowski et al. | | | | |
| 2003/0150455 A1 | 8/2003 | Bliss et al. | | | | |
| 2004/0040560 A1 | 3/2004 | Euliano et al. | | | | |
| 2004/0221848 A1 | 11/2004 | Hill | | | | |
| 2004/0221854 A1 | 11/2004 | Hete et al. | | | | |
| 2004/0231674 A1 | 11/2004 | Tanaka | | | | |
| 2004/0237963 A1 | 12/2004 | Berthon-Jones | | | | |
| 2004/0255943 A1 | 12/2004 | Morris et al. | | | | |
| 2005/0005936 A1 | 1/2005 | Wondka | | | | |
| 2005/0005938 A1 | 1/2005 | Berthon-Jones et al. | | | | |
| 2005/0034721 A1 | 2/2005 | Freitag | | | | |
| 2005/0034724 A1 | 2/2005 | O'Dea | | | | |
| 2005/0061322 A1 | 3/2005 | Freitag | | | | |
| 2005/0087190 A1 | 4/2005 | Jafari et al. | | | | |
| 2005/0098179 A1 | 5/2005 | Burton et al. | | | | |
| 2005/0121033 A1 | 6/2005 | Starr et al. | | | | |
| 2005/0121038 A1 | 6/2005 | Christopher | | | | |
| 2005/0166924 A1 | 8/2005 | Thomas et al. | | | | |
| 2005/0247308 A1 | 11/2005 | Frye et al. | | | | |
| 2006/0005834 A1 | 1/2006 | Aylsworth et al. | | | | |
| 2006/0096596 A1 | 5/2006 | Occhialini et al. | | | | |
| 2006/0124134 A1 * | 6/2006 | Wood .................. 128/207.29 | | | | |
| 2006/0149144 A1 | 7/2006 | Lynn et al. | | | | |
| 2006/0150972 A1 | 7/2006 | Mizuta et al. | | | | |
| 2006/0201504 A1 | 9/2006 | Singhal et al. | | | | |
| 2006/0243278 A1 | 11/2006 | Hamilton et al. | | | | |
| 2007/0125379 A1 | 6/2007 | Pierro et al. | | | | |
| 2007/0181125 A1 | 8/2007 | Mulier | | | | |
| 2008/0011298 A1 | 1/2008 | Mazar et al. | | | | |
| 2008/0029088 A1 | 2/2008 | Freitag et al. | | | | |
| 2008/0041371 A1 | 2/2008 | Freitag | | | | |
| 2008/0135044 A1 | 6/2008 | Freitag et al. | | | | |
| 2009/0107494 A1 | 4/2009 | Freitag et al. | | | | |

FOREIGN PATENT DOCUMENTS

| | | |
|---|---|---|
| CA | 2623756 | 3/2007 |
| CA | 2652544 | 12/2007 |
| CN | 2006-80043298.8 | 9/2006 |
| CN | 200480029872 | 11/2006 |
| CN | 2007-80022806.9 | 12/2008 |
| DE | 19626924 | 1/1998 |
| DE | 10337138.9 | 3/2005 |
| DE | 10 2006 023 637 | 11/2007 |

OTHER PUBLICATIONS

Ambrosino, "Weaning and Respiratory Muscle Dysfunction: The Egg Chicken Dilemma," Chest, 2005, vol. 128(2), pp. 481-483.

Messinger et al., "Using Tracheal Pressure to Trigger the Ventilator and Control Airway Pressure During Continuous Positive Airway Pressure Decreases Work of Breathing," Chest, 1995, vol. 108, No. 2, pp. 509-514.

Messinger et al., "Tracheal pressure triggering a demand flow CPAP system decreases work of breathing," Anesthesiology, 1994, vol. 81, A272.

Koska et al., "Evaluation of a fiberoptic system for airway pressure monitoring," J. Clin Monit, 1993, vol. 10, No. 4, pp. 247-250.

Banner et al., "Imposed work of breathing and methods of triggering demand-flow, continuous positive airway pressure system," Critical Care Medicine, 1993, vol. 21, No. 2, pp. 183-190.

Banner et al., "Site of pressure measurement during spontaneous breathing with continuous positive airway pressure: Effect on calculating imposed work of breathing," Critical Care, 1992, vol. 20, No. 4, pp. 528-533.

Sinderby et al., "Neural control of mechanical ventilation in respiratory failure", Nat Med., 1999; 5:1433-1436.

Tiep et al., "Pulsed nasal and transtracheal oxygen delivery," *Chest*, 1990, vol. 97, pp. 364-368.

Yaeger et al., "Oxygen Therapy Using Pulse and Continuous Flow With a Transtracheal Catheter and a Nasal Cannula," *Chest*, 1994, vol. 106, pp. 854-860.

Passy-Muir Inc., "Clinical Inservice Outline", Aug. 1997, revised Apr. 2004, 19 pages.

Charlotte Regional Medical Center, "Application of the Passy-Muir Tracheostomy and Ventilator", Speech-Language Pathology Department, Jan. 1995, 8 pages.

"Passy-Muir Speaking Valves," Speech Pathology Department, Nov. 13, 1998, revised May 29, 2002, 7 pages.

Prigent et al., "Comparative Effects of Two Ventilatory Modes on Speech in Tracheostomized Patients with Neuromuscular Disease," *Am J Respir Crit Care Med*, 2003, vol. 167, No. 8, pp. 114-119.

International Search Report and Written Opinion for PCT/US08/78033, dated Dec. 3, 2008.

International Search Report and Written Opinion for PCT/US08/78031, dated Nov. 24, 2008.

U.S. Appl. No. 12/153,423, filed May 19, 2008, Wondka et al.

U.S. Appl. No. 60/479,213, filed Jun. 18, 2003, Wondka.

U.S. Appl. No. 60/718,318, filed Sep. 20, 2005, Freitag et al.

U.S. Appl. No. 60/801,104, filed May 18, 2006, Freitag.

U.S. Appl. No. 60/835,066, filed Aug. 3, 2006, Freitag et al.
U.S. Appl. No. 61/071,251, filed Apr. 18, 2008, Wondka et al.
U.S. Appl. No. 61/071,252, filed Apr. 18, 2008, Wondka et al.
U.S. Appl. No. 61/091,198, filed Aug. 22, 2008, Allum et al.
U.S. Appl. No. 61/101,826, filed Oct. 1, 2008, Wondka et al.
U.S. Appl. No. 61/136,269, filed Aug. 22, 2008, Allum et al.
International Search Report and Written Opinion for PCT/US07/12108, issued Aug. 8, 2008.
Copending U.S. Appl. No. 12/153,423, filed May 19, 2008, Wondka et al.
Copending U.S. Appl. No. 12/271,484, filed Nov. 14, 2008, Freitag.
Copending U.S. Appl. No. 12/239,723, filed Sep. 26, 2008, Wondka et al.
Copending U.S. Appl. No. 12/239,719, filed Sep. 26, 2008, Wondka et al.
Copending U.S. Appl. No. 61/166,150, filed Apr. 2, 2009, Allum et al.
International Search Report and Written Opinion for PCT/US08/64015, issued Sep. 26, 2008. (co pending).
International Search Report and Written Opinion for PCT/US08/64164, issued Sep. 29, 2009. (co pending).
International Preliminary Report on Patentability for PCT/US2007/012108, issued Nov. 18, 2008. (co pending).
Copending U.S. Appl. No. 11/523,518, filed Sep. 20, 2006, Freitag et al.
Copending U.S. Appl. No. 11/523,519, filed Sep. 20, 2006, Freitag.
Copending U.S. Appl. No. 11/882,530, filed Aug. 3, 2007, Freitag.
Copending U.S. Appl. No. 60/924,514, filed May 18, 2007, Wondka et al.
Copending U.S. Appl. No. 60/960,370, filed Sep. 26, 2007, Wondka et al.
Copending U.S. Appl. No. 60/960,362, filed Sep. 26, 2007, Wondka et al.
European Search Report issued Oct. 19, 2007 in co-pending EP 04762494.
International Search Report for WO 2005/014091 (Application No. PCT/DE04/1646), filed Jan. 17, 2005.
Christopher, et al., "Transtracheal Oxygen Therapy for Refractory Hypoxemia," *JAMA*, 1986, vol. 256, No. 4, pp. 494-497.
Fink, J.B., "Helium-Oxygen: An Old Therapy Creates New Interest," *J Resp Care Pract now RT for Decision Makers in Respiratory Care*, Apr./May 1999, pp. 71-76.
Haenel, et al., "Efficacy of Selective Intrabronchial Air Insufflation in Acute Lobar Colapse," *Am J Surg*, 1992, vol. 164, No. 5, pp. 501-505.
"AARC Clinical Practice Guideline: Oxygen Therapy in the Home or Extended Care Facility," *Respiratory Care*, Aug. 1992, vol. 37, No. 8, pp. 918-922.
MacIntyre, N. R., "Long-Term Oxygen Therapy: Conference Summary," *Respiratory Care*, Feb. 2000, vol. 45, No. 2, pp. 237-245.
*VHA/DOD Clinical Practice Guideline*, "Management of Chronic Obstructive Pulmonary Disease," Ver. 1.1a, Aug. 1999, Updated Nov. 1999.
Blanch, L. L., "Clinical Studies of Tracheal Gas Insufflation," *Respiratory Care*, Feb. 2001, vol. 46, No. 2, pp. 158-166.
Gregoretti, et al., "Transtracheal Open Ventilation in Acute Respiratory Failure Secondary to Severe Chronic Obstructive Pulmonary Disease Exacerbation," *Am J Respir Crit Care Med*, 2006, vol. 173, No. 8, pp. 877-881.
Christopher, et al., "Preliminary Observations of Transtracheal Augmented Ventilation for Chronic Severe Respiratory Disease," *Respiratory Care*, Jan. 2001, vol. 46, No. 1, pp. 15-25.
Chang, et al., "Reduced Inspiratory Muscle endurance Following Successful Weaning From Prolonged Mechanical Ventilation," *Chest*, 2005, vol. 128, No. 2, pp. 553-559.
Gaughan, et al., "A Comparison in a Lung Model of Low- and High-Flow Regulators for Transtracheal Jet Ventilation," *Anesthesiology*, 1992, vol. 77, No. 1, pp. 189-199.
Menon, et al., "Tracheal Perforation. A Complication Associated with Transtracheal Oxygen Therapy," *Chest*, 1993, vol. 104, No. 2, pp. 636-637.
Rothe, et al., "Near Fatal Complication of Transtracheal Oxygen Therapy with the Scoop(R) System,"*Pneumologie*, 1996, vol. 50, No. 10, pp. 700-702. (English Abstract provided).
In the U.S. Patent and Trademark Office, Supplemental Notice of Allowance dated in re: U.S. Appl. No. 10/771,803, dated Dec. 2, 2008, 2 pages.
In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiner's Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Notice of Allowance and Examiner's Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Examiner's Interview Summary in re: U.S. Appl. No. 10/870,849, dated Jul. 27, 2007, 2 pages.
International Preliminary Report and Written Opinion on Patentability for PCT/DE2004/001646, issued Jul. 3, 2006.
International Search Report and Written Opinion for PCT/US2006/03660, issued Apr. 3, 2007.
International Search Report and Written Opinion for PCT/US2009/041034 dated Jun. 10, 2009.
In the U.S. Patent and Trademark Office, Office Action in re: U.S. Appl. No. 10/771,803, dated Jun. 14, 2007, 17 pages.
In the U.S. Patent and Trademark Office, Office Action in re: U.S. Appl. No. 11/523,519, dated Mar. 7, 2007, 12 pages.
In the U.S. Patent and Trademark Office, Final Office Action in re: U.S. Appl. No. 11/523,519, dated Nov. 26, 2007, 21 pages.
In the U.S. Patent and Trademark Office, Final Office Action in re: U.S. Appl. No. 11/523,519, dated Jul. 11, 2008, 24 pages.
In the U.S. Patent and Trademark Office, Office Action in re: U.S. Appl. No. 10/870,849, dated Feb. 22, 2007, 13 pages.
In the U.S. Patent and Trademark Office, Restriction in re: U.S. Appl. No. 10/870,849, dated Nov. 16, 2007, 5 pages.

* cited by examiner

Section A-A

FIG. 8A

Section C-C

FIG. 9A

Section B-B

FIG. 9B

TRACHEOSTOMA SPACER, TRACHEOTOMY METHOD, AND DEVICE FOR INSERTING A TRACHEOSTOMA SPACER

PRIORITY INFORMATION

This application claims priority to U.S. Provisional Patent Application Ser. No. 60/801,104 filed May 18, 2006, entitled "Tracheostomy Placeholder and Systems and Methods Relating to a Tracheostomy Placeholder," the disclosure of which is incorporated herein by reference in its entirety.

FIELD OF INVENTION

The invention relates to a tracheostoma spacer with a tubular support framework, to a tracheotomy method, and to a device for inserting a tracheostoma spacer.

DESCRIPTION OF RELATED ART

Tracheotomies are medical procedures carried out in situations where a person has to be intubated for a length of time, where malformations, diseases or injuries of the upper airways lead to acute closure, or where there is a threat of suffocation. A surgically established opening in the trachea is known as a tracheostoma. Several methods for creating such a tracheostoma are known: percutaneous dilation tracheotomy, percutaneous puncture tracheotomy, surgical tracheotomy, ENT tracheotomy, and tracheotomy in laryngectomy.

SUMMARY OF THE INVENTION

One aspect of the present invention relates to percutaneous tracheotomy methods. In these, the trachea can be punctured using a hollow needle or can be pierced using a trocar. The opening thus formed can be widened, and a tube can be finally placed in the opening. In the context of percutaneous dilation tracheotomy, a guide wire is generally first inserted into the opening, and the latter can be then widened using an inflatable balloon. Bleeding at the wound site is then staunched by pressing extremely firmly on the surrounding.

A problem of percutaneous tracheotomy methods is that the tracheostoma closes again within a very short time after removal of a cannula or tube placed in the tracheostoma, and renewed insertion is very soon found to be difficult or even impossible. For this reason, various cannulae or tubes have been developed intending to keep the tracheostoma open. A disadvantage of the known cannulae or tubes is that they are large and bulky; they protrude from the patient's neck, they extend deep into the tracheal lumen, and they have relatively thick walls and large fixed diameters. Therefore, they are obtrusive to the patient and require a relatively large tracheostoma to be made to accommodate the cannula or tube. Also they do not assist in the dilatation of the tracheostoma, and they do not conform to patient anatomy, rather the anatomy conforms to the rigidity of the cannula or tube.

One aspect of the invention is directed to a tracheostoma spacer, a tracheotomy method and a device for inserting such a tracheostoma spacer, in which the tracheostoma can be made smaller and/or does not have to be expanded as much and in which the spacer can perform some dilatation of the tracheostoma and conform to the person's anatomy.

Another aspect of the invention is achieved by a tracheostoma spacer having the features of Patent Claim 1.

This tracheostoma spacer can include a support framework that can be expanded from an initial state to a supporting state of increased diameter and has a fixing element at an end.

Accordingly, the tracheostoma spacer can be inserted in an unexpanded, compressed or crimped initial state into the tracheostoma and has a very small diameter and, after it has been fitted in place, it can be expanded or widened to a diameter corresponding to the physiological and clinical requirements, for example by an inflatable balloon or a rigid dilator or another instrument, whereupon the tracheostoma is also expanded. In this way, a spacer is provided which can be individually adapted with very little effort and has very good tolerability. The fixing element at the end, which is either arranged on the outside on the skin or on the inside in the trachea, effectively prevents the spacer from being pushed out of the trachea or from being aspirated.

Advantageous embodiments and further developments of the tracheostoma spacer are the subject of dependent Claims 2 to 32.

The support framework can also self-expand from an initial state to a supporting state of increased diameter. In this way, no active widening of the opening is needed. In one embodiment, the spring forces that the support framework possesses, because of its material and its design, are sufficient to widen the tracheostoma.

The length of the support framework can be adjustable. This permits adaptation of the tracheostoma spacer to an individual stoma depth so that the spacer is not unnecessarily long and obtrusive, but long enough to perform its function and to match the individual's anatomy. In one embodiment, the adjustability can be afforded by a two-part support framework whose component parts can be pushed one inside the other in the manner of a telescope. Self-adjusting support framework geometries are also conceivable which, through twisting, winding or tilting, permit adjustment of the length of the support framework. The length adjustment can also be effected by the spring force of the support framework. By way of a suitable structure and choice of material, the support framework can be configured such that the diameter decreases as the length increases, and vice versa—and hence the length can be self shortened after placement of the spacer in the tracheostoma in its lengthened condition. Or, the spacer length can be self shortening by shape memory elements within the support framework. For example, when brought to body temperature, the shape memory elements can contract the length of the tracheostoma spacer, for example, by the elements shortening, twisting, bending, winding, coiling or sliding. The spring shortening forces or the shape memory shortening forces are selected to not over compress the tissue surrounding the tracheostoma, but to gently compress the tissue so the spacer is secure. For example the shortening forces that allow this can be between 0.05 lbs (0.023 kg) and 0.5 lbs (0.23 kg). In this way, an anatomically correct length of the support framework is obtained to match the stoma depth.

The fixing element preferably has atraumatic edges. This ensures that the fixing element does not cut into the tissue of the trachea or otherwise irritate the tissue. The edges of the fixing element can be rounded.

In the supporting state, the fixing element protrudes beyond the outer circumference of the support framework, transversely with respect to the central longitudinal axis. In this way, an abutment is formed which effectively prevents the tracheostoma spacer from being pushed out of the tracheostoma or from being aspirated.

Fixing elements can be provided at the ends of the support framework. For example, in one embodiment, two fixing elements can be provided at one end of the support framework. The division into several fixing elements means that these can each be made smaller, and the insertion and removal of the tracheostoma spacer is facilitated. The fixing elements can advantageously be folded in for insertion and removal. In this way, the tracheostoma does not have to be made much larger than the external diameter of the support framework in the initial state.

The fixing elements at one end of the support framework can be arranged lying opposite one another. This configuration facilitates the self-alignment of the tracheostoma spacer in the trachea in order to adapt to the anatomical circumstances.

Fixing elements can be provided at one or both ends of the support framework. When at both ends, in one direction, they prevent the tracheostoma spacer from being forced out of the tracheostoma, and, in the other direction, they prevent it from being pushed or aspirated into the trachea. The tracheostoma spacer is thus secured all around.

In one embodiment, the fixing elements of one end can be offset relative to the fixing elements of the other end by a right angle about the central longitudinal axis of the support framework. The self-alignment of the tracheostoma spacer in the tracheostoma is advantageously supported by this arrangement. The fixing elements located in the trachea will orient themselves in the vertical direction, since the trachea is concave on the inside. Correspondingly, the fixing elements on the outer surface of the skin will align themselves in the horizontal direction, so that forward and backward movements of the head are not impeded by the tracheostoma spacer. In addition, it is conceivable for the tracheostoma spacer to provide a supporting function in the trachea.

In one embodiment, the fixing element can have an aperture. The aperture advantageously makes it easier to grip the tracheostoma spacer, for example in order to remove it from the tracheostoma. The aperture can be, for example, circular, oval or elliptic.

The support framework can have tubular guide elements. Such tubular guide elements facilitate the insertion of tubes which are needed for delivery of gas, including, for example, oxygen, to the lungs or for aspiration of mucus from the lungs and from the trachea. The tubular guide elements preferably extend out beyond one end of the support framework. This end is intended to lie in the trachea and is further intended to be preferably curved or can have a shoulder in order to deflect the tubes in the direction of the lungs. The tube can thus be inserted into the trachea such that it is at a desired spacing from the posterior wall of the trachea and does not abut the posterior wall or otherwise irritate the tracheal mucosa. The tubular guiding element can also be used to allow the tracheostoma spacer to slide with the proper alignment on the tracheotomy device.

Moreover, the support framework is assigned a valve unit. With the valve unit, it is advantageously possible to inhale through the tracheostoma and exhale through the trachea. The patient is still able to speak in some cases. In addition, instruments can be pushed from outside through the tracheostoma. The valve unit for this purpose can either be pushed in from the outside or can be a structural part of a jacket of the support framework. In the second solution, part of the jacket would be designed as a duckbill-shaped membrane.

In a further embodiment, the support framework can be assigned a humidifier. In this way, the respiratory air drawn into the lungs is humidified. The humidifier consists of a shaped article which is able to store moisture during exhalation and is able to release this during inhalation.

A coupling element can be provided for fixing articles that are passed through or inserted into the support framework. Such articles are, for example, the valve unit, the humidifier or a tube.

The support framework can be enclosed by a jacket. By way of the jacket, the tissue adjoining the tracheostoma spacer can be protected and the insertion and removal of the tracheostoma spacer can be made easier, because the jacket provides, among other things, an advantageous increase in the sliding ability of the tracheostoma spacer. For this purpose, the jacket can also comprise a hydrophobic or hydrophilic slide-promoting coating. The jacket also prevents adherence of the adjoining tissue to the tracheostoma spacer. The jacket can have a nano-molecular coating. The jacket can also be made from a polymer. In this way, the expandable support framework is not impeded in its expansion. The jacket can additionally contain pharmaceutical active substances which have an anti-inflammatory action or serve to protect against bacteria or microbes, or can contain tissue growth modulators or regulators in order to prevent growth of granulomas or to promote endothelialization. Further suitable active substances are, for example, saline solutions, wound ointments and lidocaine (a local anaesthetic). The active substances can be provided in the form of fluids.

The support framework can also be provided with a reservoir which has an opening on the outer circumferential face of the support framework, and/or a channel which has one end on the circumferential face of the support framework. The fluids can be introduced into the reservoir. Through the opening, the fluids are able to reach the outer circumferential face, so that they can act directly on the adjoining tracheostoma tissue, thus facilitating the insertion and removal of the tracheostoma spacer and generally improving its tolerability. By way of the channel, the fluids can be injected as and when required and in the necessary amount.

The support framework can have a circular cross section. This configuration can be advantageous from the point of view of production engineering. However, the support framework can also have an oval cross section. Other cross-sectional shapes are of course also conceivable in the context of the invention. These cross-sectional shapes permit an adaptation to the anatomy of the trachea, in particular to the surrounding rings of cartilage. Moreover, the support framework can have an indentation and/or a bulge in its cross section. A kidney-shaped cross section is also conceivable.

The support framework can be constructed and/or manufactured in a variety of ways in accordance with conventional principles and techniques. For example, the support framework can be woven, braided, laser cut from a tube or a combination of these and other ways of making the support framework. For example, in one embodiment, the support framework can have struts made of filaments. Thus, a support framework can be obtained whose diameter can be varied. The filaments can be made of metal, for example. A shape-memory alloy, for example nitinol, is particularly suitable. The construction from metal facilitates the spring-elastic self-expansion of the support framework and increases the service life of the tracheostoma spacer. By using a shape-memory alloy, the change in diameter can additionally be effected in a temperature-controlled manner.

The support framework can also comprise woven synthetic filaments. Such a support framework can advantageously be produced by a die-casting or extrusion process. The filaments can also be coated with an elastomer.

The wall thickness of the support framework, preferably, can be smaller than one fifth, preferably smaller than one tenth, of the external diameter of the support framework in the supporting state. A thin wall thickness has the advantage that the tracheostoma can be kept small. The smaller the tracheostoma, the quicker and better the opening heals after removal of the tracheostoma spacer. In one embodiment, the tracheostoma spacer can have two concentric support frameworks, an outer support framework being placed permanently or semi-permanently in the opening in the trachea, and an inner support framework being intended to be withdrawn from the outer support framework at defined intervals and cleaned.

In another aspect of the invention, the method can be achieved by a tracheotomy method comprising the steps in Patent Claim 33. For this purpose, a tracheostoma (an opening in the trachea) is first established, and a tracheostoma spacer of expandable diameter is then placed in the opening in the trachea.

Advantageous embodiments of the tracheotomy method are the subject of dependent Claims 34 to 37.

The opening through the skin and tracheal wall can be formed using a needle knife, scalpel or trocar. Cutting avoids tearing of the tracheostoma tissue, which tearing results in poorer healing of the tissue and the formation of larger or thicker scars. The incision for forming the opening in the trachea is in this case made transversely with respect to the trachea. This is anatomically advantageous, since the cartilage rings that surround the trachea are also oriented in this direction.

Before the tracheostoma spacer is fitted in place, the opening in the trachea, if desirable and/or necessary, can be widened using an instrument which is rigid or whose diameter can be widened, for example a balloon dilator.

In another aspect of the invention, the device part can be achieved by a device used for creating the opening and for inserting a tracheostoma spacer and having the features of Patent Claim 38.

The device can include a cutting instrument on whose shaft the tracheostoma spacer can be placed, and a cover sleeve can be movable on the shaft over a tracheostoma spacer that has been placed there.

The device can be used to pierce the trachea or to produce an incision in the trachea and can then be introduced into the resulting opening in the trachea. After the position of the device has been verified by bronchoscopy, the cover sleeve is drawn back, so that a tracheostoma spacer placed under the cover sleeve expands from an initial state to a supporting state of increased diameter and the fixing elements deploy. The device for inserting the tracheostoma spacer is then removed again from the opening. Using this device for inserting a tracheostoma spacer permits a minimally invasive and rapid placement of the spacer.

Additional embodiments and developments of the device are the subject of dependent Claims 39 to 51.

The cutting instrument can have a conical tip. Such a tip can advantageously widen the tracheostoma upon insertion of the device.

The cutting instrument can have channel for a guide wire. Before the incision is made, the guide wire can be introduced percutaneously into the trachea and then can be inserted or threaded into the channel. In this way, the accuracy of the positioning of the tracheal incision and of the tracheostoma spacer is increased.

The cutting instrument can comprise a needle. The trachea can be advantageously punctured using the needle.

The cutting instrument additionally or alternatively can comprise a knife, a scalpel, or a trocar. An advantageous horizontal incision in the trachea can be made with these instruments.

A cuff can be arranged on the cover sleeve. Such a cuff is annular and inflatable. With the cuff, the tracheostoma can be additionally widened if so required.

The shaft can have a magazine section. In the magazine section, the diameter of the shaft is reduced, so that a tracheostoma spacer can be placed at this location and, during the insertion process, can be fixed in place in the initial state.

The shaft also has a guide section, which can advantageously permit the movement of the cover sleeve on the shaft.

The shaft and the cover sleeve can be curved. In this way, adaptation to the anatomical circumstances can be permitted and the insertion of a tracheostoma spacer is made easier. The shaft and the cover sleeve are expediently curved along the longitudinal axis.

The cross section of the device is adapted to an opening in the trachea. The cross section is therefore not necessarily circular, but can also be oval and/or have an indentation and/or bulge.

In another aspect of the invention, a grip surface can be provided. This can permit firm manual gripping of the device. The grip surface can have a surface structure.

The device also can include a safety element. Provision can be made so that the cutting instrument can be retracted into a housing. This minimizes the risk of injury and the danger of incorrect incisions. For retracting the cutting instrument, an actuating element, for example in the form of a press button, is provided at the free end near the grip surface.

An abutment can also be provided at the tip of the cutting instrument or on the cover sleeve and prevents the device from being pushed into the trachea beyond a defined depth. Damage to the posterior wall of the trachea can be advantageously prevented by the abutment.

An instrument for removal and/or reinsertion of the tracheostoma spacer is also provided. The instrument can be inserted into the support framework. Gripper elements, which can preferably spread in the longitudinal direction of the instrument, then engage in at least one section of the support framework and/or a fixing element. The tracheostoma spacer is then shortened in length and reduced in diameter. In this way, the tracheostoma spacer detaches itself from the surrounding tissue and can be withdrawn with the instrument from the opening in the trachea. This method can be employed in the reverse sequence, in order to reinsert the tracheostoma spacer in the opening of the trachea.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. Accordingly, the invention is explained in more detail below with reference to illustrative embodiments depicted in the drawings.

DETAILED DESCRIPTION OF PREFERRED EMBODIMENTS

Identical or similar features in the drawings are provided with identical reference labels.

Figure 1:
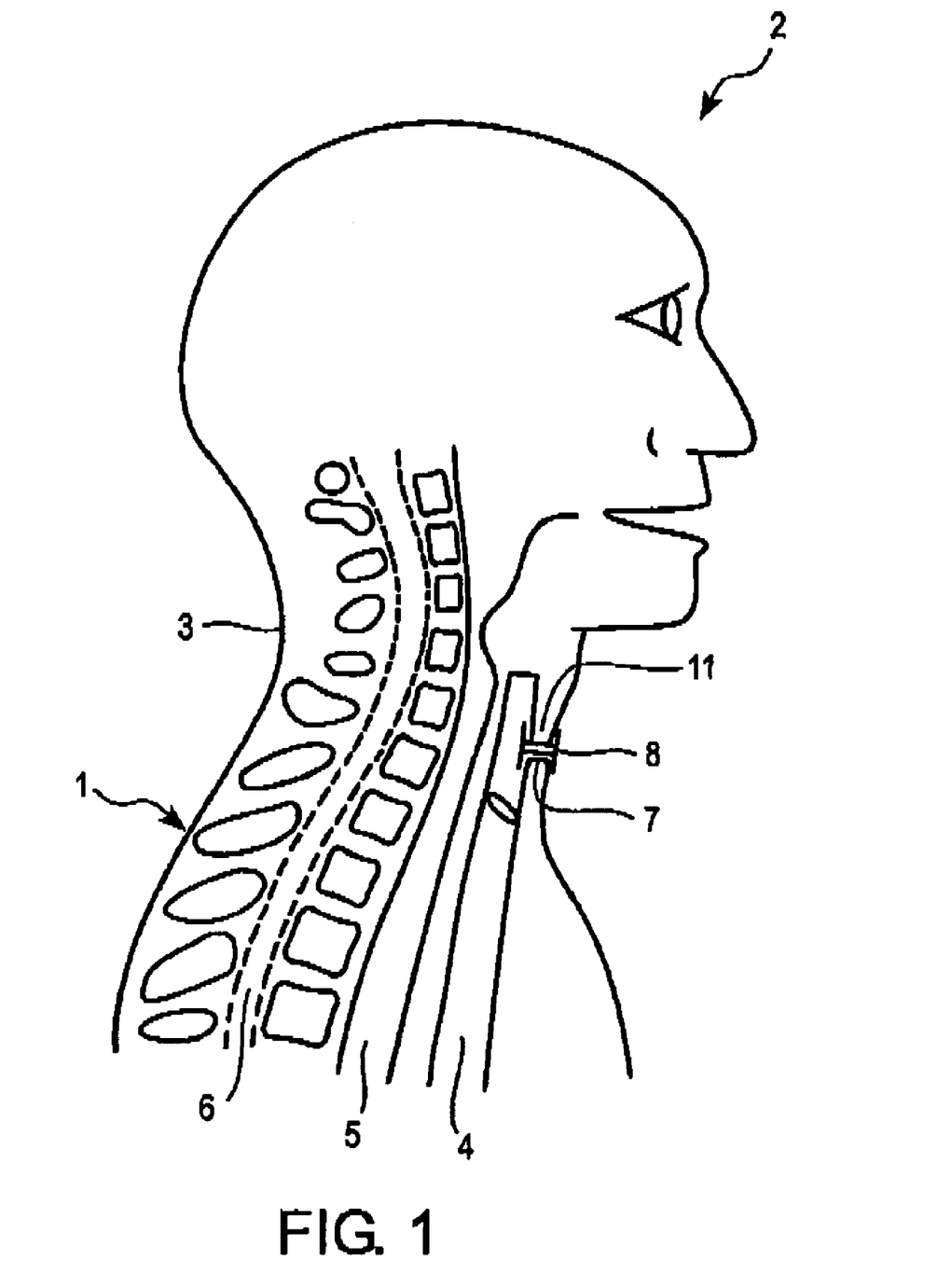
FIG. 1 shows a schematic partial section through the upper body of a human including an embodiment of a tracheostoma spacer in accordance with the principles of the invention.

A schematic partial section through the upper body 1 of a patient 2 is shown in FIG. 1. In the region of the neck 3, the trachea 4 is preferably situated in front of the oesophagus 5 and the spinal column 6. To help the patient 2 breathe, a percutaneous tracheotomy has been performed in which an opening in the trachea 4 has been made through the skin, this opening being referred to as a tracheostoma 7. To prevent the tracheostoma 7 from quickly closing again, a tracheostoma spacer 8 according to the invention is positioned in the tracheostoma 7.

Figure 2:
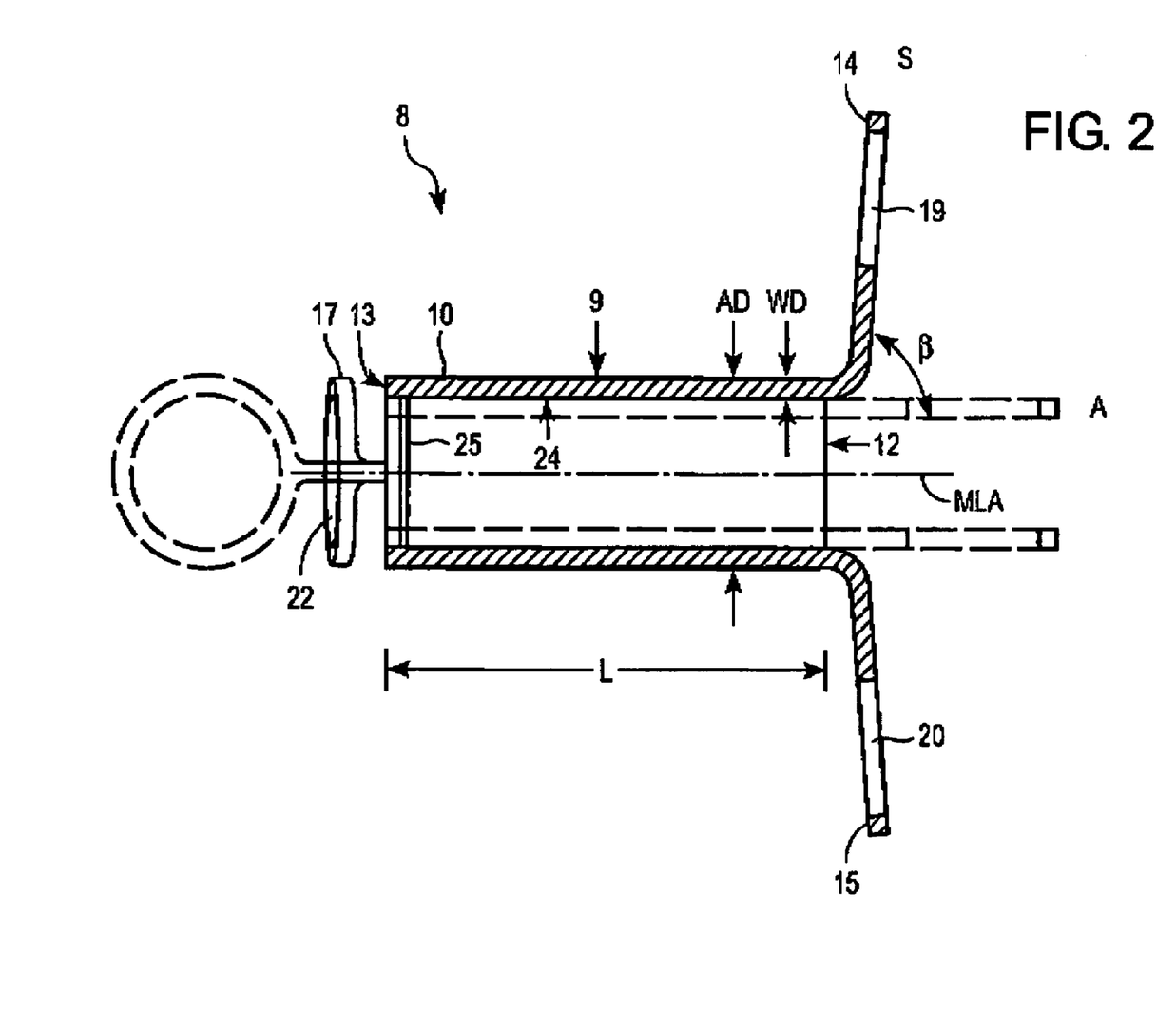
FIG. 2 shows an embodiment of a tracheostoma spacer in the unexpanded state (dashed lines) and the expanded state in cross section (solid lines).
Figure 3:
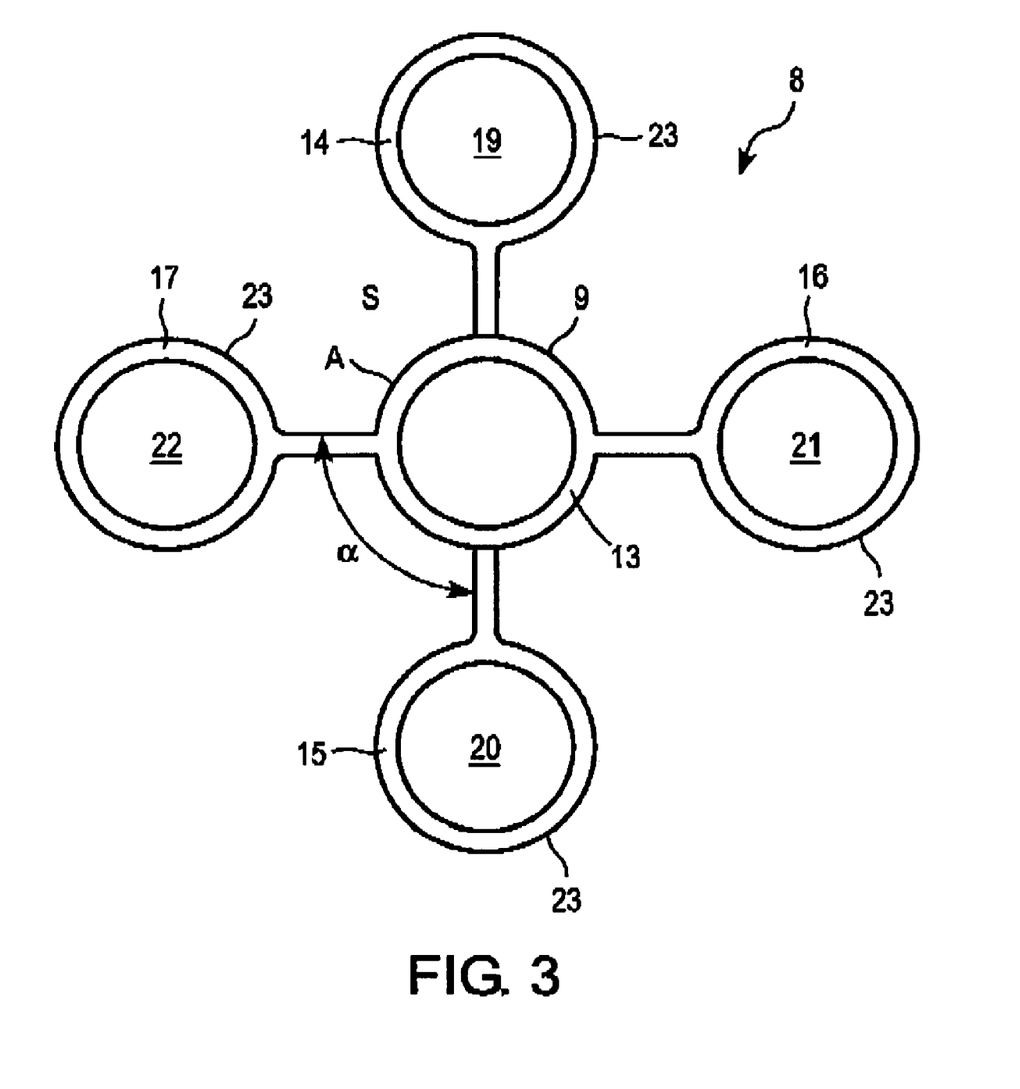
FIG. 3 shows the tracheostoma spacer of FIG. 2 in a side view from the front end.

The tracheostoma spacer 8 is shown in more detail in FIGS. 2 and 3. The tracheostoma spacer 8 has a tubular support framework 9. The support framework 9 is able to self-expand from an initial state A (shown by broken lines) to a supporting state S of increased diameter (shown by solid lines). The length L of the support framework can be adjustable. For example, to be able to adjust the length L of the support framework 9, the support framework can be configured and/or constructed to be adjustable. In one embodiment an adjustment means can be provided in the framework, such as but not limited to a telescoping feature, twisting, winding, or tilting of elements in the framework, or a spring force or shape memory behaviour of the framework or elements in the framework.

The support framework 9 can be surrounded by a jacket 10 made from a polymer. The jacket can facilitate the insertion and removal of the tracheostoma spacer 8 and can avoid injuries to the adjacent tissue 11 (see FIG. 1). The jacket 10 can also contain pharmaceutical active substances which have an anti-inflammatory action and serve to protect against bacteria.

The support framework 9 can have a circular cross section and can then be cut particularly easily from a tubular semi-finished product, for example. The support framework 9 can be composed of struts (not shown in detail) in the form of filaments. The filaments can be made from a shape-memory alloy, in particular from a nickel-titanium alloy, also referred to as nitinol, for example.

To keep the tracheostoma 7 as small as possible (see FIG. 1), it is preferable to have the support framework 9 with a thin wall thickness. For example, in one embodiment, the wall thickness WD of the support framework 9 can be less than one tenth (1/10) of the external diameter AD of the support framework 9 in the supporting state S.

At both ends 12, 13 of the support framework 9, fixing elements 14-17 can be provided that allow the tracheostoma spacer 8 to be fixed in place in the trachea 4. In the supporting state S, the fixing elements 14-17 can be bent at an angle β of 80° to 100°, for example, and protrude beyond the outer circumference A of the support framework 9. In one embodiment, two fixing elements 14, 15; 16, 17, respectively, can be provided at each end 12, 13 and can be arranged lying opposite one another. The fixing elements 14, 15 of one end 12 can be offset relative to the fixing elements 16, 17 of the other end 13 by a right angle α around the central longitudinal axis MLA of the support framework 9. To improve the handling of the tracheostoma spacer 8 during its insertion and removal, the fixing elements 14-17 can have circular apertures 19-22 which make it easier to grip the tracheostoma spacer 8, for example with a hook-shaped instrument. The fixing elements 14-17 preferably have atraumatic edges 23 which are rounded and polished.

Provided on the inside face 24 of the support framework 9, there also can be a coupling element 25 in the form of a peripheral groove. The coupling element 25 forms an abutment for fixing a valve unit inserted into the support framework 9 or for fixing a humidifier, or for fixing a tube which has been pushed through and is also referred to as a catheter.

Figure 4:
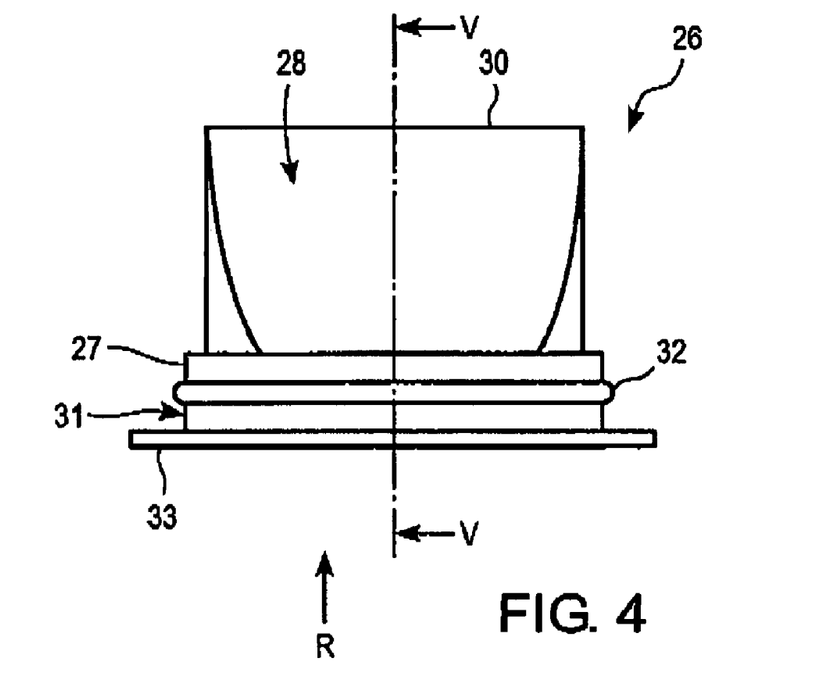
FIG. 4 shows an embodiment of a valve unit in a side view.
Figure 5:
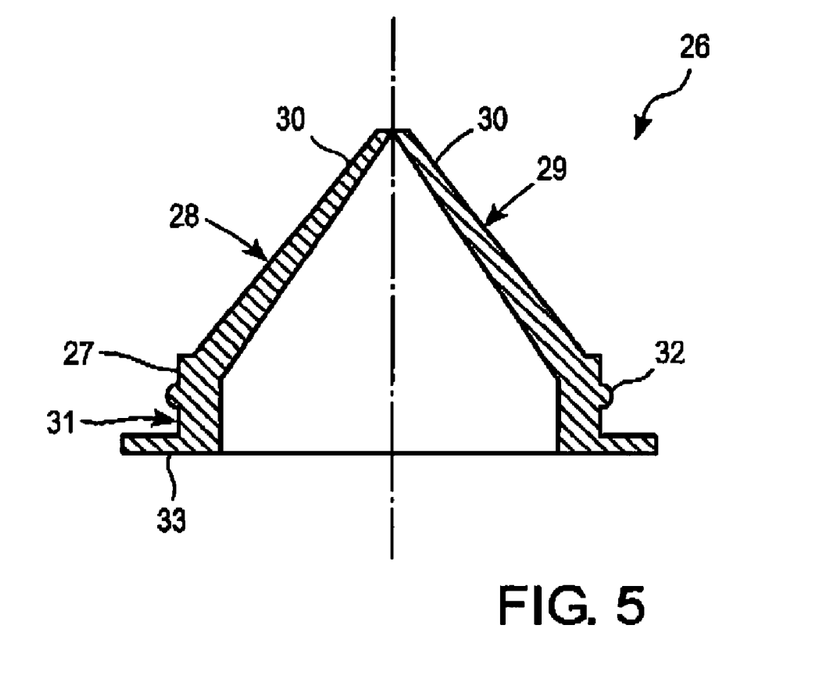
FIG. 5 shows the valve unit in cross section along the line V-V in FIG. 4.

A valve unit 26 is shown by way of example in FIGS. 4 and 5. The valve unit 26 has a sleeve-shaped middle section 27 which can be adjoined by two beak-shaped lips 28, 29. Each lip 28, 29 can have a flat portion 30 which is thin and flexible so that respiratory air can be inhaled through the valve unit 26 in the direction R with only very slight resistance. In the opposite direction, the valve unit 26 is closed during exhalation. A further advantage of this valve unit 26 is that tubes and similar articles can also be inserted in direction R through the valve unit 26. A coupling element 32 in the form of a peripheral spring can be arranged on the outer circumferential surface 31 of the sleeve-shaped section 27. At its end, the valve unit 26 has a peripheral collar 33.

Figure 6:
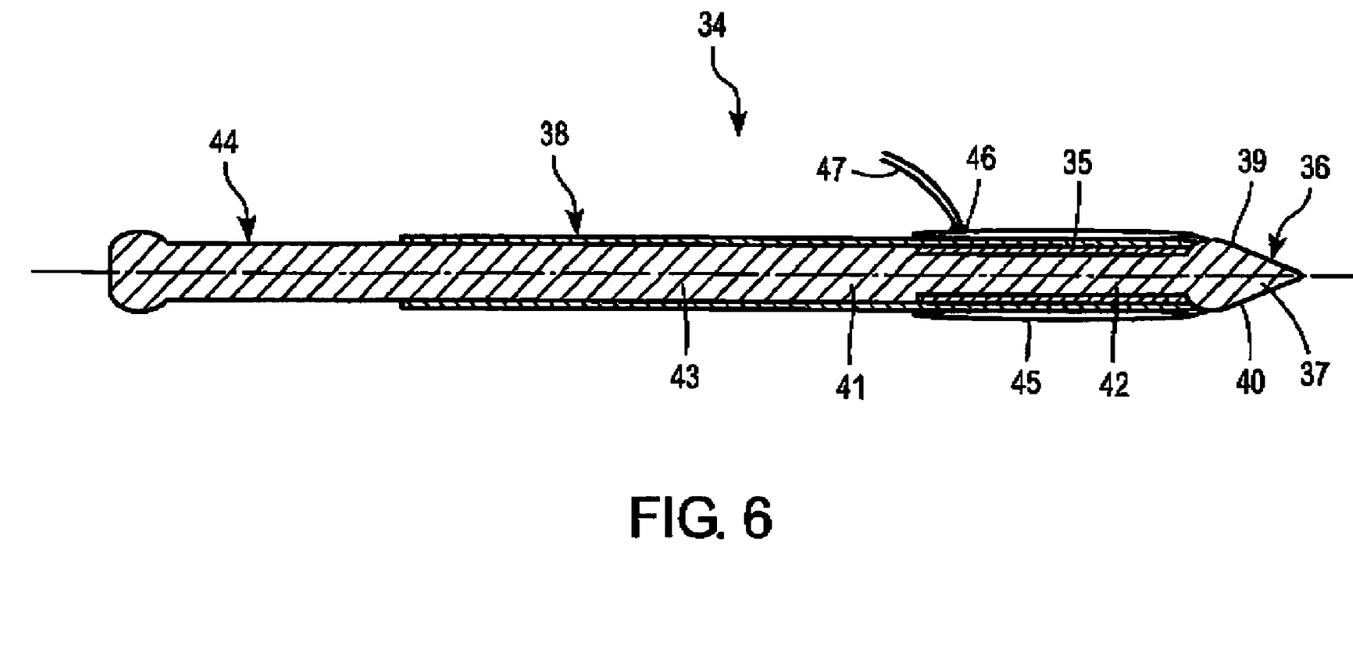
FIG. 6 shows a cross section of an embodiment of a device for inserting a tracheostoma spacer, the tracheostoma spacer being placed under the cover sleeve.

A device 34 for inserting a tracheostoma spacer 8 is shown in FIG. 6. This device 34 is a rigid surgical instrument which can include an internal cutting instrument 36 in the form of a trocar 37 and, arranged outside this, a cover sleeve 38. The trocar 37 can have two very sharp edges 39, 40 with which an opening can be cut in the trachea. The trocar 37 is arranged on a shaft 41. Behind the trocar 37, there is a magazine section 42 of narrower diameter on which a tracheostoma spacer 8 is placed. This is adjoined by a guide section 43 of greater diameter. The cover sleeve 38 can be moved by sliding on the guide section 43 of the shaft 41 and can be pushed over the tracheostoma spacer 8 and can hold the latter in the initial state during insertion. At its end, the shaft 41 can have a grip surface 44.

To be able to widen the tracheostoma, a cuff 45 can be arranged on the periphery of the cover sleeve 38 and can be filled with a fluid. For this purpose, the cuff 45 has suitable connector elements 46 for a tube 47.

The device 34 for inserting the tracheostoma spacer 8 can make the positioning of the tracheostoma spacer 8 much quicker and simpler. The trachea simply can be punctured to a small diameter in advance. The device 34 is then inserted and the correct position in the tracheostoma is verified by bronchoscopy. The cover sleeve 38 is then drawn back, and the tracheostoma spacer 8 expands, and the fixing elements also deploy. Finally, the device 34 simply can be removed again from the opening.

The tracheostoma spacer 8, according to the invention permits a minimally invasive tracheotomy. The radially acting forces during the self-expansion of the tracheostoma spacer 8, cause a widening of the tracheostoma 7, so that other auxiliary devices can generally be dispensed with. The tracheostoma has a small diameter and heals within a very short time after removal of the tracheostoma spacer 8.

Figure 7:
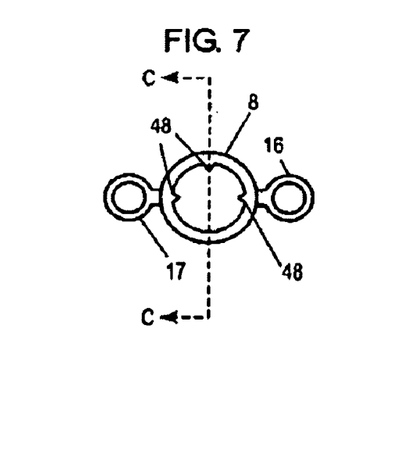
FIG. 7 shows an end view of another embodiment of a tracheostoma spacer in accordance with the principles of the invention.

FIG. 7 describes a front view of the tracheostoma spacer 8 after insertion into a person. The fixing elements 16, 17 can be seen oriented 180 degrees apart oriented side to side. In this figure, the tube guiding elements 48 are depicted as protrusions from the inner wall of the tracheostoma spacer, however this is exemplary only and the guiding elements can take a variety of forms. The tube guiding elements can serve to orient another device, which is to be inserted into the tracheostoma spacer, in the proper orientation. Examples of another device to be inserted into the tracheostoma spacer include but are not limited to a catheter 51, the tracheotomy device 34, a tracheostoma spacer removal tool, or an instrument.

Figure 8A:
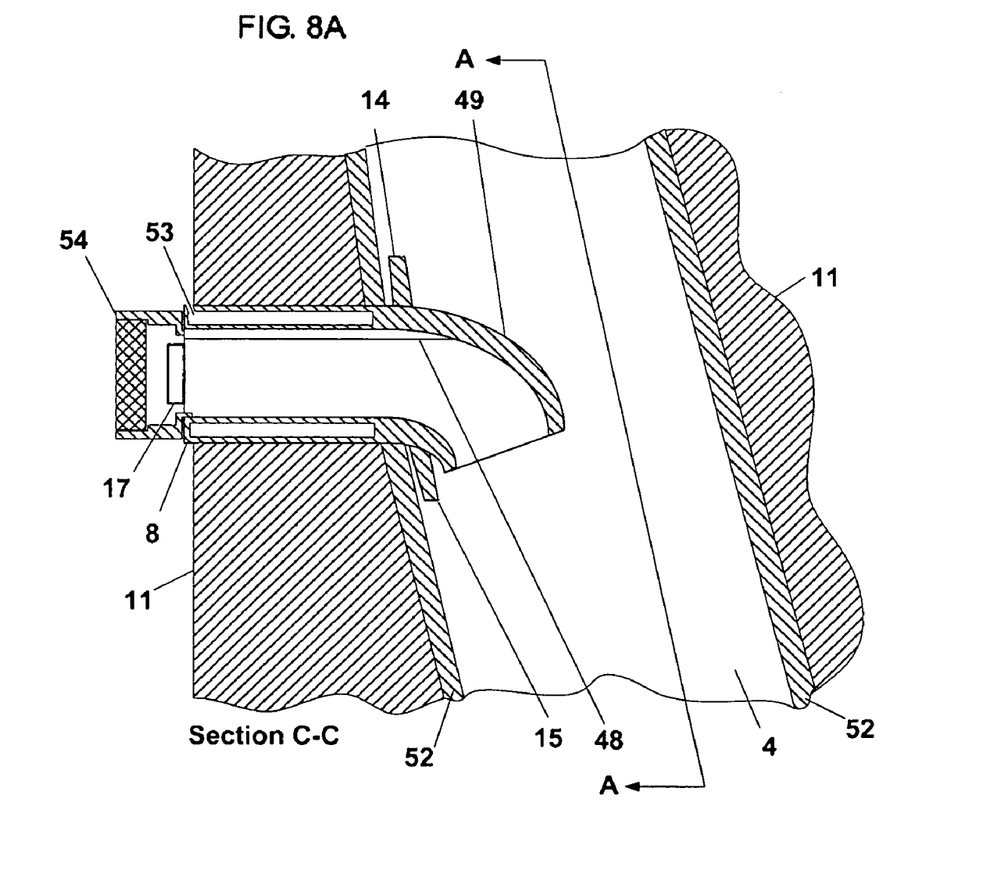
FIG. 8A shows a cross-sectional view along line C-C of the tracheostoma spacer of FIG. 7 in situ.
Figure 8B:
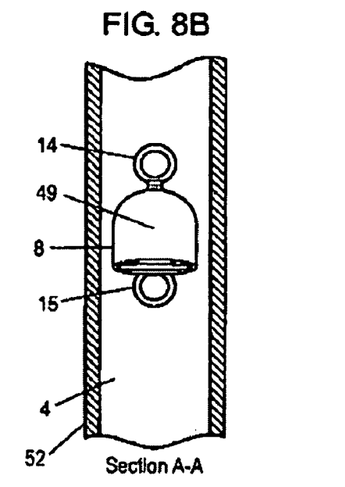
FIG. 8B shows a partial section view in situ where the tracheostoma spacer of FIG. 7 is viewed from inside the trachea.

Referring to FIG. 8A, the tracheostoma spacer 8 from FIG. 7 is shown in a cross section in the person's tissue 11, trachea 4, and tracheal wall 52. A fixing element 17 on the outside or proximal side is shown as well as the fixing elements 14, 15 on the inside or distal side, the latter oriented 180 degrees apart and 90 degrees from the proximal side fixing elements. A tube guiding element 48 is shown as well as a tube guiding curve 49, which can serve to guide the device being inserted downward toward the lung. Also the tube guiding curve 49 can serve to position the device being inserted in the desired position, for example away from the posterior or anterior tracheal wall to avoid unnecessary or undesired contact with the tracheal wall 52. Although tube guiding curve 49 can function as a safety element, other types of safety elements can be provided in accordance with the principles of the invention.

Figure 9A:
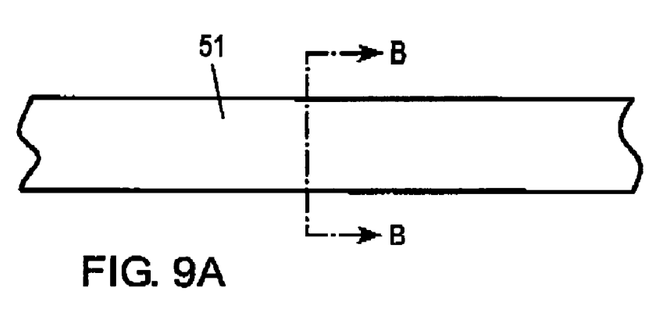
FIG. 9A shows a side of an embodiment of a catheter in accordance with the principles of the invention.
Figure 9B:
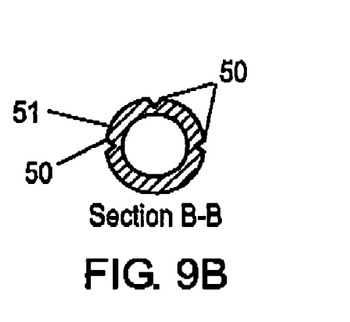
FIG. 9B shows a cross sectional view of the catheter taken along line B-B in FIG. 9.

Referring to FIG. 9, an exemplary catheter 51 is described which is intended to be inserted into the tracheostoma spacer. Examples of catheters are, but not limited to: a ventilation catheter, oxygen therapy cannula, suction catheter, diagnostic catheter, a drug delivery catheter, sampling catheter or a fiberoptic catheter. As described in Section B-B (FIG. 9B) guiding elements 50 are described which mate with the tube guiding elements 48 on the tracheostoma spacer (FIG. 7). The guiding elements 50 are shown in exemplary form only and can comprise a variety of forms and shapes. A catheter is described in this embodiment as an example, however the same principles can apply to other devices to be inserted into the tracheostoma spacer, such as but not limited to the tracheotomy device 34, a tracheostoma spacer removal tool, or an instrument.

LIST OF REFERENCE NUMERALS 1 upper body
2 patient
3 neck
4 trachea
5 oesophagus
6 spinal column
7 tracheostoma
8 tracheostoma spacer
9 support framework
10 jacket
11 tissue
12 end of 9
13 end of 9
14 fixing element
15 fixing element
16 fixing element
17 fixing element
19 aperture
20 aperture
21 aperture
22 aperture
23 edge
24 inside face of 9
25 coupling element
26 valve unit
27 sleeve-shaped section of 26
28 lip
29 lip
30 flat section of 28, 29
31 circumferential surface
32 coupling element
33 collar
34 Tracheotomy device
36 cutting instrument
37 trocar
38 cover sleeve
39 edge of 37
40 edge of 37
41 shaft
42 magazine section
43 guide section
44 grip surface
45 cuff
46 connector elements
47 tube
48 Tube Guiding Element
49 Tube Guiding Curve
50 Guiding Element
51 Catheter
52 Tracheal Wall
A outer circumference
AD external diameter
L length
MLA central longitudinal axis
R direction
WD wall thickness
α right angle
β angle Although the preferred embodiments are directed to tracheostomy, the principles of the invention can be applied to other fields, in particular, for example, other types of ostomies including colon, or other access devices including vascular.

Moreover, although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A tracheostoma spacer comprising a tubular support framework, wherein the tubular support framework is able to expand from an initial state to a supporting state of increased diameter and comprises at least one fixing element at least one end; and wherein the tubular support framework comprises at least one tubular guide element to guide a tracheotomy device or a catheter to be inserted through the tracheostoma spacer.

2. The tracheostoma spacer according to claim 1, wherein the tubular support framework is able to self-expand from the initial state to the supporting state of increased diameter.

3. The tracheostoma spacer according to claim 1, wherein a length of the tubular support framework is adjustable.

4. The tracheostoma spacer according to claim 1, wherein at least on of the at least one the fixing element has atraumatic edges.

5. The tracheostoma spacer according to claim 1, wherein, when the tubular support framework is in the supporting state, at least one of the at least one fixing element protrudes beyond an outer circumference of the tubular support framework, transversely with respect to a central longitudinal axis of the tubular support framework.

6. The tracheostoma spacer according to claim 1, wherein wherein at least one end of the tubular support framework comprises at least two fixing elements.

7. The tracheostoma spacer according to claim 6, wherein the at least two fixing elements are arranged opposite one another.

8. The tracheostoma spacer according to claim 1 wherein the tubular support framework comprises at least two ends, wherein each of the at least two ends of the support framework comprises a pair of fixing elements.

9. The tracheostoma spacer according to claim 8, wherein the pair of fixing elements of one end of the tubular support framework are offset relative to the pair of fixing elements of the other end of the tubular support framework by a right angle about a central longitudinal axis of the support framework.

10. The tracheostoma spacer according to claim 1, wherein the fixing element has an aperture.

11. The tracheostoma spacer according to claim 1, wherein at least one of the at least one tubular guide element extends beyond an end of the support framework.

12. The tracheostoma spacer according to claim 1, wherein at least one of the at least one tubular guide element is curved.

13. The tracheostoma spacer according to claim 1, wherein the support framework comprises at least one valve unit.

14. A tracheostoma spacer comprising a tubular support framework, wherein the tubular support framework is able to expand from an initial state to a supporting state of increased diameter and comprises at least one fixing element at least one end; and further comprising a coupling element for fixing articles passed through or inserted into the support framework.

15. The tracheostoma spacer according to claim 1, wherein the support framework comprises a jacket.

16. The tracheostoma spacer according to claim 15, wherein the jacket comprises a polymer.

17. The tracheostoma spacer according to claim 15, wherein the jacket contains pharmaceutical active substances.

18. A tracheostoma spacer comprising a tubular support framework, wherein the tubular support framework is able to expand from an initial state to a supporting state of increased diameter and comprises at least one fixing element at least one end; and further comprising a channel which has one end on a circumferential face of the support framework.

19. The tracheostoma spacer according to claim 1, wherein the support framework has a circular cross section.

20. The tracheostoma spacer according to claim 1, wherein the support framework has an oval cross section.

21. A tracheostoma spacer comprising a tubular support framework, wherein the tubular support framework is able to expand from an initial state to a supporting state of increased diameter and comprises at least one fixing element at least one end; and wherein the support framework comprises an indentation in its cross section.

22. The tracheostoma spacer according to claim 1, wherein the support framework comprises a bulge in its cross section.

23. The tracheostoma spacer according to claim 1, wherein the support framework comprises struts made of filaments.

24. The tracheostoma spacer according to claim 23, wherein the filaments are made of metal.

25. The tracheostoma spacer according to claim 23, wherein the filaments are made of a shape-memory alloy.

26. The tracheostoma spacer according to claim 1, wherein the support framework comprises woven synthetic filaments.

27. The tracheostoma spacer according to claim 23, wherein the filaments are coated with an elastomer.

28. The tracheostoma spacer according to claim 1, wherein a wall thickness of the support framework is smaller than one fifth (⅕) of an external diameter in the supporting state.

29. The tracheostoma spacer according to claim 1, wherein a wall thickness of the support framework is less than one tenth (1/10) of an external diameter in a supporting state.

30. A tracheotomy method comprising the following steps: forming an opening in the trachea; and placing a tracheostoma spacer in the opening of the trachea; where in the tracheostoma spacer comprises a tubular support framework, wherein the tubular support framework is able to expand from an initial state to a supporting state of increased diameter and comprises at least one fixing element at least one end; and wherein the tubular support framework comprises at least one guide element to guide a tracheotomy device or catheter to be inserted through the tracheostoma spacer.

31. The tracheotomy method according to claim 30, wherein the opening of the trachea is punctured using a needle or a trocar.

32. The tracheotomy method according to claim 30, wherein the opening of the trachea is cut with a knife or a scalpel.

33. The tracheotomy method according to claim 32, wherein an incision for forming the opening of the trachea is made transversely with respect to the trachea.

34. The tracheotomy method according to claim 30, wherein, before the tracheostoma spacer is placed in the opening in the trachea, the opening in the trachea is widened using an instrument which is rigid.

35. The tracheostoma spacer according to claim 1, wherein at least one of the at least one tubular guide element has a shoulder.

36. The tracheostoma spacer according to claim 1, wherein the catheter is a ventilation catheter.

37. The tracheostoma spacer according to claim 6, wherein the at least two fixing elements protrude beyond an outer circumference of the support framework.

38. The tracheostoma spacer according to claim 6, wherein the at least two fixing elements comprise two fixing elements that are rotationally spaced approximately 180 degrees apart from one another.

39. The tracheostoma spacer according to claim 8, wherein, in each pair of fixing elements, the two fixing elements are rotationally spaced approximately 180 degrees apart from one another.

40. The tracheostoma spacer according to claim 1, wherein the tracheotomy device is adapted to insert the tracheostoma spacer into a stoma.

41. The tracheostoma spacer according to claim 1, wherein the tracheotomy device comprises a cutting instrument.

42. The tracheostoma spacer according to claim 41, wherein the cutting instrument is selected from the group consisting a conical tip, a trocar, a needle, a scalpel, and a knife.

43. The tracheostoma spacer according to claim 41, wherein the cutting instrument comprises a channel for a guidewire.

44. The tracheostoma spacer according to claim 1, wherein the tracheotomy device comprises a cover sleeve.

45. The tracheostoma spacer according to claim 44, wherein the tracheotomy device comprises a cuff arranged on the cover sleeve.

46. The tracheostoma spacer according to claim 1, wherein the tracheotomy device comprises a safety element adapted to prevent over-insertion of the instrument into a trachea.

47. The tracheostoma spacer according to claim 1, wherein the tracheotomy device comprises a dilator.

48. The tracheostoma spacer according to claim 1, wherein the tracheostoma spacer is adapted to be placed over a shaft of the tracheotomy device.

49. The tracheostoma spacer according to claim 13, wherein at least one of the at least one valve unit is adapted to open to allow a flow of gas in at least one direction.

50. The tracheostoma spacer according to claim 13, wherein at least one of the at least one valve unit is adapted to open to allow the passage of a catheter through the opening.

51. The tracheostoma spacer according to claim 26, wherein the filaments are coated with an elastomer.

52. The tracheostoma spacer according to claim 1, wherein at least one of the at least one fixing element is ring-shaped and has at least one flat face, and wherein one of the at least one flat face is adapted to lie against tissue of a patient when the tracheostoma spacer is inserted into a stoma of a patient and the support framework is in the supporting state.

53. The tracheostoma spacer according to claim 1, wherein at least one of the at least one fixing element is collapsible to facilitate insertion into a stoma, and is expandable into a protruded state.

54. The tracheotomy method according to claim 30, wherein, before the tracheostoma spacer is placed in the opening in the trachea, the opening in the trachea is widened using an instrument whose diameter can be widened.

\* \* \* \* \*